United States Patent [19]

Lyons

[11] 3,962,294
[45] June 8, 1976

[54] OLEFIN ISOMERIZATION CATALYSTS AND PROCESS

[75] Inventor: James E. Lyons, Wallingford, Pa.

[73] Assignee: Sun Ventures, Inc., St. Davids, Pa.

[22] Filed: May 9, 1975

[21] Appl. No.: 575,872

Related U.S. Application Data

[60] Continuation-in-part of Ser. No. 391,895, Aug. 27, 1973, abandoned, which is a division of Ser. No. 251,986, May 10, 1972, Pat. No. 3,855,323, which is a continuation-in-part of Ser. No. 80,750, Oct. 14, 1970, abandoned.

[52] U.S. Cl. ..................... 260/429 R; 252/429 R; 252/431 P; 260/666 A; 260/666 PY; 260/683.2

[51] Int. Cl.² ........................................ C07F 15/00

[58] Field of Search ................................. 260/429 R

[56] References Cited

OTHER PUBLICATIONS

Lupin et al., J. Chem. Soc. (A) 1968, pp. 741–749.

Primary Examiner—Arthur P. Demers
Attorney, Agent, or Firm—J. Edward Hess; Donald R. Johnson; Stanford M. Back

[57] ABSTRACT

The activity of olefin isomerization catalysts such as $RuCl_2(Ph_3P)_3$ may be substantially enhanced in the presence of compounds which are readily decarbonylated by $RuCl_2(Ph_3P)_3$ to form carbonyl derivatives of said catalysts.

5 Claims, No Drawings

OLEFIN ISOMERIZATION CATALYSTS AND PROCESS

RELATED APPLICATIONS

This application is a continuation in part of U.S. Ser. No. 391,895, filed Aug. 27, 1973, now abandoned which in turn is a divisional application of U.S. Ser. No. 251,986, filed May 10, 1972, now U.S. Pat. No. 3,855,323 which in turn is a continuation-in-part of U.S. Ser. No, 80,750, filed Oct. 14, 1970, now abandoned.

BACKGROUND OF THE INVENTION

This invention relates to novel olefin isomerization catalysts, and to methods for preparing and using the same. More particularly, this invention relates to an improved method for isomerizing olefins and diolefins in the presence of novel metal carbonyl catalysts formed by reacting certain ruthenium complexes with compounds which are readily decarbonylated in the presence of said complexes. This invention is also directed to the novel metal carbonyl catalysts themselves.

It is known that such compounds as $RuCl_2(Ph_3P)_3$ are catalysts for the isomerization of olefins. See, for example, Abley et al. Disc. of Farady Soc., 46, 31, 37 (1968). These reactions, however, are often characterized by very slow reaction rates, thus making such processes commercially impracticable.

There is also taught, in U.S. Pat. No. 3,530,198, a process for the preparation of olefins from carboxylic acids or their esters comprising contacting said acid or ester with a catalyst comprising a Group VIII metal complexed with an organometallic ligand of phosphorus, arsenic or antimony, to form olefins, carbon monoxide and water or alcohol. However, notwithstanding the presence of CO, olefin and organometallic catalyst in the reaction medium of this process, no increase in isomerization rate or selectivity is obtained when employing the acid or ester starting materials of this patented process in conjunction with the olefins of the present invention, as demonstrated by certain comparative examples set forth below. Moreover, as these examples will also demonstrate, none of the carbonyl complex comprising the novel catalyst of this invention is formed when this prior art method is employed.

SUMMARY OF THE INVENTION

It has now been found, in accordance with the present invention, that the rate and selectivity of olefin isomerization metal complex catalysts of the formula

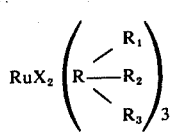

wherein X is halogen; and $R_1$, $R_2$ and $R_3$ are a lower alkyl having from 1 to 6 carbon atoms, a cycloalkyl group or an aryl (i.e. phenyl, tolyl, naphthyl, etc.) group, and wherein $R_1$, $R_2$ and $R_3$ may be the same or different, may be substantially enhanced by reacting said complexes with organic compounds which are readily decarbonylated by said complexes (i.e. "CO-donating compounds") to form novel carbonyl derivatives thereof. These carbonyl derivatives thereof. These carbonyl derivatives formed from said metal complexes and said compounds which are decarbonylated are metal carbonyl complexes having the formula

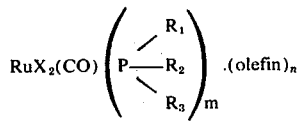

wherein X and $R_1$, $R_2$ and $R_3$ are as defined above, and m and n are 2 or 3 , and 0 or 1 respectively, but when $m$ is 3, $n$ is 0; and when $m$ is $2n$ can be 0 or 1, depending upon the olefin or the compound which is decarbonylated. It is these carbonyl compounds which comprise the improved olefin isomerization catalyst of this invention.

These improved catalysts are advantageous in that they permit the isomerization reaction to be carried out at a rapid rate in a highly selective manner under mild conditions in the absence of air or oxygen which tends to deactivate the ruthenium metal complexes over a period of time. The yields obtained are, in most instances, substantially quantitative.

These novel catalysts and process are particularly advantageous in that they provide a homogeneous reaction medium under mild conditions to give rapid but selective double-bond isomerization reactions wherein the double bond shifts take place in a stepwise manner. In addition, skeletal rearrangements, polymerization and other undesirable side reactions do not occur to any detectable extent.

Thus, for example, despite the dramatic rise in the reaction rates there is no loss in selectivity in these isomerizations. For example, cycloalkadienes which are prone to disproportionation when conventional catalysts are used (acid, base, heterogeneous metal and some soluble catalysts), are smoothly and rapidly isomerized, as shown in Equations 1 and 2. Similarly, vinyl-substituted cyclic hydrocarbons, as shown in Equations 3, 4 and 5, which are prone to give many isomers as well as disproportionation products, are isomerized to a single exocyclic olefin:

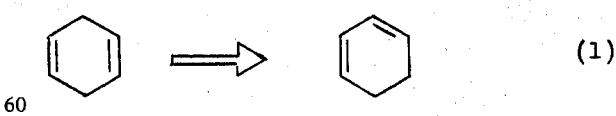 (1)

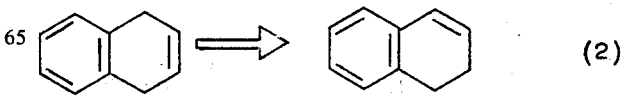 (2)

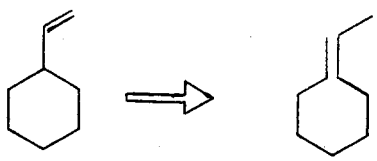

(3)

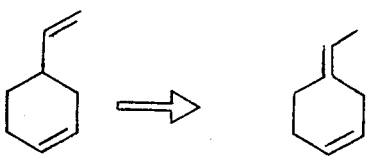

(4)

(5)

DESCRIPTION OF THE INVENTION

The novel catalysts of this invention may be conveniently formed and the isomerization process carried out by first dissolving the aforedescribed ruthenium metal complex in the olefin which is to be isomerized, followed by addition of the CO-donating compound to form the metal carbonyl catalysts in situ. The reaction mixture is then heated at a temperature of from about 70° to 140°C, and preferably from 90° to 100°C for from 12 to 28 hours, and most preferably from 16 to 20 hours, under an inert atmosphere such as nitrogen or helium. The reaction product may readily be recovered from the reaction mixture by vacuum distillation or like methods, leaving the catalyst material which may then be used again in its existing form without further treatment.

It will be understood, of course, that while it is more convenient to form the metal carbonyl catalyst of this invention in situ in the olefin starting material as described above, it is also contemplated that said catalyst may be formed separately in a suitable olefin and then added to the reaction medium.

The olefin starting materials employed in carrying out this process include any isomerizable monoolefin having from 4 to 36 carbon atoms, or diolefin having from 5 to 40 carbon atoms, as for example the following monoolefins and diolefins:

Monoolefins:

pentene-1
hexene-1, hexene-2
heptene-1, heptene-2
octene-1, octene-2
vinylcyclohexane
vinylcyclopentane
vinylcycloheptane
allylcyclohexane
allylcyclopentane
nonene-1
decene-1, decene-2, decene-3
4-methylcyclohexene-1
4-methylcyclopentene-1
4-methylcyclooctene-1
allylbenzene
propenylbenzene
4-phenylbutene-1

Diolefins:

1,4-cyclohexadiene
1,4-cyclooctadiene, 1,5-cyclooctadiene
4-vinylcyclohexene-1
1,4-cycloheptadiene
1,4-dihydronaphthalene
1,4-pentadiene
1,4-hexadiene
1,4-octadiene 1,5-octadiene, 1,6-octadiene
2-methyl-1,4-pentadiene
5-phenyl-1,4-pentadiene
de-limonene and like isomerizable olefins.

The aforementioned metal complexes include compounds having the formula

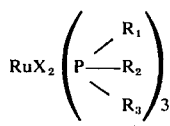

wherein X and $R_1$, $R_2$ and $R_3$ are as defined above. Of these, the ruthenium compounds of the formula $RuCl_2(Ph_3P)_3$ are preferred, wherein Ph is phenyl. The molar concentration of metal complex to be used in accordance with the invention is not critical, but it desirably in the range of from $10^{-2}$ to $10^{-4}$ moles of catalyst per liter of olefin, and preferably about $10^{116\ 3}$ moles. Larger amounts may be employed but are not necessary.

The organic CO-donating compounds are, as mentioned above, those compounds which decarbonylate readily in the presence of the above metal complexes to form carbonyl derivatives of said metal complexes. Included amongst those materials are carbon monoxide, ethylene oxide, styrene oxide, butadiene monoxide, phenylacetaldehyde, benzaldehyde, crotonaldehyde, epoxides, formic acid esters such as benzyl formate, alcohols and related materials. However, other carboxylic acids than formic acid, such as acetic acid and higher homologues thereof, and their esters, are not effective CO-donating compounds for purposes of this invention. When carbon monoxide is employed as the carbonyl compound, it is desirable to bubble a stream of this gas through the olefin prior to addition of the metal complex. The amount and manner in which carbon monoxide is added should be carefully regulated to avoid formation of a catalytically inactive dicarbonyl complex. Generally, however, the molar concentration of the carbonyl-donating compounds may vary from $10^{-1}$ to $10^{-3}$ moles of compound per liter of olefin, and preferably about $10^{-2}$ moles.

In a further embodiment of this invention, it has been found that ruthenium complexes having arsine ligands may be substituted for the ruthenium phosphine complexes described above as starting materials in the preparation of the improved catalysts of this invention. Thus, it has been found that complexes of the formula

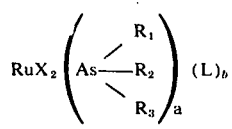

wherein X and $R_1$, $R_2$ and $R_3$ are as defined above, L is a low molecular weight alcohol or ketone such as methanol, ethanol, acetone or the like, $a$ is 2 to 4, and $b$ is 0 or 1, when contacted in the same manner and with the same organic compounds described above which are readily decarbonylated to form effective olefin isomerization catalysts of the formula

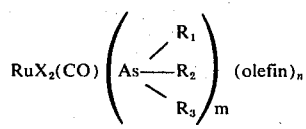

wherein X, $R_1$, $R_2$ and $R_3$ are as defined above, and wherein m and n are 2 or 3, and 0 or 1, respectively, but when m is 3, n is 0; and when m is 2, n can be 0 or 1, depending upon the olefin or the compound which is decarbonylated.

These above-described ruthenium arsine complexes used in the preparation of the improved catalysts of this invention are prepared by contacting a ruthenium halide with the respective substituted arsine compound in a lower molecular weight alcohol or ketone solvent. Thus, depending upon the precise nature of the $R_1$, $R_2$ and $R_3$ compounds as well as the solvent employed, the number of arsine groups and "L" groups will vary accordingly.

The following examples are provided to illustrate the novel processes and products of this invention.

EXAMPLE 1

Carbon monoxide was bubbled rapidly through pure 4-vinylcyclohexene (free of oxygen or hydroperoxides) for 30 seconds. The 4-vinylcyclohexene had been purified by distillation under nitrogen followed by percolation through activated silica gel under nitrogen. The olefin, 10 ml., was added to 0.062 gm. of [$RuCl_2(Ph_3P)_3$] and the mixture stirred under nitrogen for 18.5 hours. After this time the reaction mixture was allowed to cool to room temperature and g.l.p.c. analysis showed 23.2 percent isomerization has occured (see Table I for isomer distribution). A similar experiment carried out in the absence of CO gave less than 1.5 percent isomerization after 20 hours. Introduction of CO, therefore, gave a 15-fold increase in the percent of isomerization.

An orange complex (m.p.=190°C dec.) having the following composition:

$RuCl_2(CO)(PPh_3)_2 \cdot (C_8H_{12})$ was precipitated in 40 percent yield (0.025 gm) after reaction by adding 50 ml. of n-pentane to the reaction mixture. The infrared spectrum [$\nu CO=5.1\mu(vs); \nu Ph_3P=9.1\mu(s)$] showed that this material was a carbonyl complex. It was capable of isomerizing pure 4-vinylcyclohexene at a rapid rate even in the absence of added CO. The results of this run are summarized in Table I.

EXAMPLE 2

According to the procedures of Example 1, ethylene oxide was bubbled through 10 ml. of pure 4-vinylcyclohexene for 30 seconds prior to addition of 0.062 gm. [$RuCl_2(Ph_3P)_3$]. After stirring at 100°C under nitrogen for 19.5 hours g.l.p.c. analysis showed that 99.8 percent isomerization had occurred as compared with <1.5 percent without ethylene oxide. Addition of 50 ml. n-pentane to the reaction mixture precipitated 0.0062 gm. (10 percent yield) of a brown soild having absorptions in the infrared at 5.1 and 9.1 characteristic of Ru—CO and —$PPh_3$ respectively. The results of this run are summarized in Table I.

EXAMPLE 3

A 5 × $10^{-2}$M solution of styrene oxide (10 ml.) in pure (cf. Example 1) 4-vinycyclohexene was added to 0.062 grams of [$RuCl_2(Ph_3P)_3$] and the solution stirred at 100°C under nitrogen for 29 hours. Glpc analysis showed that the extent of isomerization was 99 percent. Addition of pentane to the reaction mixture gave a tan solid having infrared absorptions at 5.1 (Ru-CO) and 9.1 ($Ph_3P$). The results of this run are summarized in Table I.

EXAMPLE 4

According to the procedure of Example 3, 0.1 ml. of benzylformate, 10.0 ml. of 4-vinylcyclohexene, and 0.062 gm. [$RuCl_2Ph_3$]$_3$ were stirred at 100°C under nitrogen for 19 hours. Isomerization was complete and products are listed in Table I. Addition of 50 ml. pentane to the reaction mixture gave 0.036 gm. (58 percent yield) of a tan carbonyl $\nu[\mu(CO)=5.0\mu(s); \nu(Ph_3P)=9.1\mu(s)]$ which decomposed from 137° to 147°C. The results of this run are summarized in Table I.

EXAMPLES 5 to 12

In accordance with the general procedures of the foregoing examples, but varying the olefin substrate, the CO-donating catalyst, together with the quantities of catalyst and the reaction times, there were obtained the results tabulated below in Table I as Examples 5 to 12, along with the tabulation of the results of Examples 1 to 4.

In Example 11, the catalyst complex which was formed from $RuCl_2(Ph_3P)_3$, allylbenzene ($C_9H_{10}$), and CO, was isolated in 40 percent yield and identified as

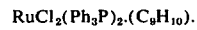

$RuCl_2(Ph_3P)_2 \cdot (C_9H_{10})$.

TABLE I

The Effect of CO, Aldehydes and Epoxides on Olefin Isomerization by $RuCl_2(Ph_3P)_3$

| Ex. No. | Olefin | Co-Catalyst | Time (Hrs.) | Temp (°C) | Ru(II) (M/L)$^a$ | Co-Cat. (M/L)$^a$ | Products, (%) | Isomerization (%) | Ruthenium Complex After Reaction | | | |
|---|---|---|---|---|---|---|---|---|---|---|---|---|
| | | | | | | | | | Color | IR | m.p. (°C) | Yield(%) |
| 1 | 4-VCH$^e$ | CO | 18.5 | 100 | 6.6×10$^{-3}$ | $^a$ | trans-4-ECH, 7.8; cis-4-ECH,7.7; trans-3-ECH, 1.0; cis-4-ECH,1.0; Other, 5.7 | 23.2 | Orange | 5.1μ(vs) 9.1μ(s) | ~190 dec. | 40 |
| 2 | " | Ethylene oxide | 19.5 | 100 | 6.6×10$^{-3}$ | $^a$ | trans-4-ECH, 0.2; cis-4-ECH,0.3; trans-3-ECH, 41.1; | 99.8 | Brown | 5.1μ(m) 9.1μ(vvs) | $^c$ | 10 |

TABLE I-continued

The Effect of CO, Aldehydes and Epoxides on Olefin Isomerization by $RuCl_2(Ph_3P)_3$

| Ex. No. | Olefin | Co-Catalyst | Time (Hrs.) | Temp (°C) | Ru(II) (M/L)[d] | Co-Cat. (M/L)[d] | Products, (%) | Isomerization (%) | Color | IR | m.p. (°C) | Yield(%) |
|---|---|---|---|---|---|---|---|---|---|---|---|---|
| 3 | " | Styrene oxide | 29.0 | 100 | $6.6 \times 10^{-3}$ | $5 \times 10^{-2}$ | cis-4-ECH, 52.8; ethylcyclohexadiene, 4.5; Other, 0.9 | 99.0 | Tan | 5.1μ(vs) | [c] | [c] |
| | | | | | | | cis+trans-ECH, 1.4; trans-3-ECH, 41.5; cis-4-ECH, 51.1; Other, 4.8 | | | | | |
| 4 | 4-VCH | Benzyl-formate | 19.0 | 100 | $6.6 \times 10^{-3}$ | $8 \times 10^{-2}$ | cis+trans-4-ECH, 0.3; trans-3-ECH, 43.3; cis-3-ECH, 53.9; Other, 2.5 | 99.8 | Tan | 5.0μ(s) 9.1μ(s) | 137–147 dec. | 58 |
| 5 | 4-VCH[e] | None | 18 | 100 | $6.6 \times 10^{-3}$ | — | trans-4-ECH[f], 0.7; cis-4-ECH, 0.7; Other, 0.1 | 1.5 | Gold | 6.4μ(m) 9.1μ(s) (doublet) | 110–113 → clear melt | 46 |
| 6 | " | Phenyl-acetaldehyde[b] | 19.5 | 100 | $6.6 \times 10^{-3}$ | $5 \times 10^{-2}$ | trans-4-ECH, 12.2; cis-4-ECH, 14.6; trans-3-ECH, 13.5; cis-3-ECH, 15.6; Other, 7.9 | 63.5 | Tan | 5.1μ(s) (doublet) 9.1 | [c] | 59 |
| 7 | " | Croton-aldehyde | 29.0 | 100 | $6.6 \times 10^{-3}$ | $1 \times 10^{-1}$ | trans-4-ECH, 3.5; cis-4-ECH, 3.3; cis+trans-3-ECH, 0.9; Other, 1.5 | 9.2 | Tan | 5.1μ(vs) 9.1μ(s) 6.1, 6.2(w) | [c] | [c] |
| 8 | Allyl-benzene | None | 17.0 | 100 | $1 \times 10^{-2}$ | — | cis-propenyl-benzene, 1.6; trans-propenyl-benzene, 3.7; Other, 0.2 (indane) | 5.5 | Green Brown | 9.1(s) | ~225 dec. | [c] |
| 9 | " | Ethylene oxide | 19.0 | 100 | $1 \times 10^{-2}$ | [a] | cis-propenyl-benzene, 5.5; trans-propenyl-benzene, 93.9; Other, 0.1 | 99.5 | Tan | 5.1μ(vs) 9.1μ(vs) | [c] | 10 |
| 10 | " | Styrene oxide | 17.5 | 100 | $6.6 \times 10^{-3}$ | $5 \times 10^{-2}$ | cis-propenyl-benzene, 5.0; trans-propenyl-benzene, 94.6; Other, 0.2 | 99.8 | Green | 5.1μ(m) 9.1μ(vs) | >300 | 15 |
| 11 | " | CO | 17.0 | 100 | $1 \times 10^{-2}$ | [a] | cis-propenyl-benzene, 24.1; trans-propenyl-benzene, 28.5; Other, 1.3 (indane) | 53.9 | Red-Brown | 5.1μ(vs) 9.1μ(s) | 270–277 | 40 |
| 12 | 4-VCH | Benz-aldehyde | 17.0 | 100 | $6.6 \times 10^{-3}$ | $9 \times 10^{-2}$ | trans-4-ECH, 3.7; cis-4-ECH, 4.2; trans-3-ECH, 0.4; cis-3-ECH, 0.5; Other, 2.5 | 11.3 | Dark tan | 5.1μ(vs) 9.1μ(s) | | 33 |

[a]Administered by bubbling the gas rapidly through the olefin for several minutes prior to addition of catalyst
[b]50 percent solution in ethanol
[c]This data was not obtained
[d]M/L = moles/liter
[e]VCH = vinylcyclohexene
[f]ECH = ethylidenecyclohexene

EXAMPLE 13

In accordance with the general procedures of Example 4, 0.062 gms. of $RuCl_2(PEt_2Ph)_3$, where Et is ethyl and Ph is phenyl, is stirred together with 10 ml. of 1-hexene under nitrogen atmosphere at 64PC in the presence of 0.5 ml. of ethanol for 48 hours. At the end of that period analysis of the reaction product by glpc shows that a mixture of isomeric hexenes is obtained in good yield, and the complex, $RuCl_2(CO)(PEt_2Ph)_2 \cdot (C_6H_{12})$, where $C_6H_{12}$ corresponds to the hexene moiety, is isolated in the usual manner.

EXAMPLE 14

In accordance with the foregoing procedure, but substituting $RuCl_2(Ph_3As)_2(CH_3OH)$ for $RuCl_2(PEt_2Ph)_3$, there is obtained the same mixture of isomeric hexenes in good yield.

EXAMPLE 15

In accordance with the procedures of Example 2, vinylcyclopentane was isomerized to ethylidenecyclopentane (98 percent) and 1,4-dihydronaphthalene was isomerized to 1,2-dihydronaphthalene (99 percent).

In the former case the complex, RuCl$_2$(CO)(PPh$_3$)$_2$.(C$_7$H$_{12}$), where C$_7$H$_{12}$ corresponds to the ethylidenecyclopentane moiety, is isolated after reaction in the usual manner.

EXAMPLE 16

In comparison with the selective formation of 1,2-dihydronaphthalene (99 percent) from 1,4-dihydronaphthalene as demonstrated in Example 15, above, when the conditions and starting materials of Example 1 of U.S. Pat. No. 3,530,198 are applied to this compound, the following results are obtained:

To 0.5 g palladium chloride, 3 g. triphenylphosphine and 100 g. octanoic acid is added 10 mls. of 1,4-dihydronaphthalene and the mixture refluxed according to the procedures of Example 1 of U.S. Pat. No. 3,530,198. In addition to the octenes obtained from dicarboxylation, there is observed the formation of 1,2-dihydronaphthalene — 38 percent, decalin — 22 percent, naphthalene — 28 percent and others — 12 percent. It is noted that substantial amounts of palladium metal is deposited in the reaction flask.

The following three examples also illustrate the difference in the results obtained, particularly in the rates to isomerization, when the process of the present invention is compared with that of U.S. Pat. No. 3,530,198. Thus, the results of Examples 18 and 19, employing one of the carboxylic acids and esters thereof of that patent in the process of the present invention, when compared with the results obtained in Example 17, show that the prior art method yields only 5 to 6 percent in a given period while the instant method yields more than 99 percent for the same period.

Moreover, no carbonyl complex was recovered from the reaction medium of Examples 17 and 18.

EXAMPLE 17

The catalyst, RuCl$_2$(Ph$_3$P)$_3$, (0.05 h), was dissolved in 10 ml of 4-vinylcyclohexene to which 50 ml of a CO-donor (enumerated below) was added. After warming the mixture at 90°C for 24 hours the extent of isomerization to 3- and 4-ethylidenecyclohexene was determined by glpc analysis. The results are tabulated below.

| Catalyst (50 mg) | Additive (50 l) | Temp. (°C.) | % Reaction 4-VCH (10 ml) 24 hours |
|---|---|---|---|
| RuCl$_2$(Ph$_3$P)$_3$ | None | 90 | 5 |
| " | Benzylformate | 90 | 99 |
| " | Styrene oxide | 90 | 99 |

Analysis showed 58 percent of ruthenium carbonyl complex to be present when benzyl formate was used as the additive.

EXAMPLE 18

The catalyst, RuCl$_2$(Ph$_3$P)$_3$, (0.05 g), was dissolved in 10 ml of 4-vinylcyclohexene to which various amounts of octanoic acid were added. After warming the mixture at 90°C and 120°C, respectively, for 24 hours the extent of isomerization to 3- and 4-ethylidenecyclohexene was determined by glpc analysis. The results are tabulated below.

| Catalyst (50 mg.) | Acid | Temp. (°C.) | % Reaction 4-VCH (10 ml) 6 hours | 24 hours |
|---|---|---|---|---|
| RuCl$_2$(Ph$_3$P)$_3$ | None | 90 | 1 | 5 |
| " | 5 μl | 90 | 1 | 4 |
| " | 10 μl | 90 | 1 | 6 |
| " | 50 μl | 90 | 1 | 3 |
| " | 10 mls | 90 | 0 | 0 |
| " | 10 mls | 120 | 0 | 1 |

Analysis failed to reveal the presence of any organometallic ruthenium carbonyl complex.

EXAMPLE 19

The catalyst, RuCl$_2$(Ph$_3$P)$_3$, (0.05 g), was dissolved in 10 ml of 4-vinylcyclohexene to which various amounts of ethyl octanoate were added. After warming the mixture at 90°C for 24 hours the extent of isomerization to 3- and 4-ethylidenecyclohexene was determined by g.l.p.c. analysis. The results are tabulated below.

| Catalyst (50 mg.) | Ester | Temp. (°C.) | % Reaction 4-VCH (10 ml) 6 hours | 24 hours |
|---|---|---|---|---|
| RuCl$_2$(Ph$_3$P)$_3$ | None | 90 | 1 | 5 |
| " | 10 μl | 90 | 1 | 6 |
| " | 50 μl | 90 | 0.5 | 1.5 |
| " | 10 ml | 90 | 2 | 4 |

Analysis failed to reveal the presence of any organometallic ruthenium carbonyl complex.

The invention claimed is:

1. A compound having the formula

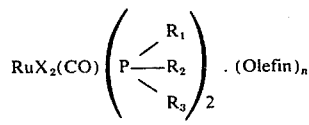

wherein X is halogen; R$_1$, R$_2$, and R$_3$ are lower alkyl groups having from 1 to 6 carbon atoms, cycloalkyl, or aryl, wherein R$_1$, R$_2$, and R$_3$ may be the same or different; and $n$ is 1; and wherein the olefin is an isomerizable monoolefin having from 4 to 36 carbon atoms or diolefin having from 5 to 40 carbon atoms.

2. A compound according to claim 1 having the formula

RuCl$_2$ (CO) (P Ph$_3$)$_2$ . (C$_8$H$_{12}$)

wherein pH is phenyl.

3. A compound according to claim 1 having the formula

RuCl$_2$ (CO) (P Ph$_3$)$_2$ . (C$_9$H$_{10}$)

wherein pH is phenyl.

4. A compound according to claim 1 having the formula

RuCl$_2$ (CO) (P Et$_2$ Ph)$_2$ . (C$_8$H$_{12}$)

wherein Et is ethyl and Ph is phenyl.

5. A compound according to claim 1 having the formula

RuCl$_2$ (CO) (P Ph$_3$)$_2$ . (C$_7$H$_{12}$)

wherein pH is phenyl.

* * * * *